United States Patent [19]
Hargreaves et al.

[11] Patent Number: 4,799,496
[45] Date of Patent: Jan. 24, 1989

[54] GUIDE WIRE HANDLE

[75] Inventors: Thomas E. Hargreaves, Mound; Donald W. Hanson, Chanhassen, both of Minn.

[73] Assignee: Lake Region Manufacturing Company, Inc., Chaska, Minn.

[21] Appl. No.: 57,108

[22] Filed: Jun. 3, 1987

[51] Int. Cl.$^4$ .................................... A61M 25/00
[52] U.S. Cl. .................... 128/772; 128/657; 604/95
[58] Field of Search ............... 128/772, 657, 656, 658, 128/344; 604/95, 164, 170, 280–283

[56] References Cited

U.S. PATENT DOCUMENTS

| | | | |
|---|---|---|---|
| 3,416,531 | 12/1968 | Edwards | 128/772 X |
| 3,452,740 | 7/1969 | Muller | 128/772 |
| 3,521,620 | 7/1970 | Cook | 128/772 |
| 3,552,384 | 1/1971 | Pierie et al. | 128/657 |
| 3,847,140 | 11/1974 | Ayella | 128/772 |
| 3,854,473 | 12/1974 | Matsuo | 128/772 X |
| 4,456,017 | 6/1984 | Miles | 128/772 |
| 4,509,945 | 4/1985 | Kramann et al. | 128/657 X |
| 4,548,206 | 10/1985 | Osborne | 128/772 |
| 4,554,929 | 11/1985 | Samson et al. | 128/772 |
| 4,600,014 | 7/1986 | Beraha | 128/754 |
| 4,759,827 | 7/1988 | Buchbinder et al. | 128/772 |

FOREIGN PATENT DOCUMENTS 0820830   4/1981   U.S.S.R. .................... 128/772

Primary Examiner—Kyle L. Howell
Assistant Examiner—Angela D. Sykes
Attorney, Agent, or Firm—Clayton R. Johnson

[57] ABSTRACT

A guide wire handle for selectively stiffening a guide wire and releasably locking the guide wire in a stiffened condition that includes a main body that can be held by one hand and has a rectangular opening in which there is mounted a slide member that is movable between a guide wire datum position and a guide wire stiffened position. The main body and slide member have elongated linear slits and bores with or without metal plate extended therein. A sleeve on the core wire proximal end abuts against the slide member plate and the proximal end of the coil spring abuts against the main body plate such that as the slide member a plate is moved away from the body plate, the coil spring is compressed and the core wire is placed in tension to stiffen the guide wire. The slide member and main body include cooperating locking parts for releasably retaining the slide member in the guide wire stiffen condition and is operable by the same hand holding the handle to an unlocked condition whereby the guide wire moves the slide member relative to the main body to the guide wire nearly fully relaxed condition. The slide member also includes a spring part to resiliently retain the slide member in a datum position while permitting movement against the resilient action to facilitate loading the handle with the guide wire.

29 Claims, 2 Drawing Sheets

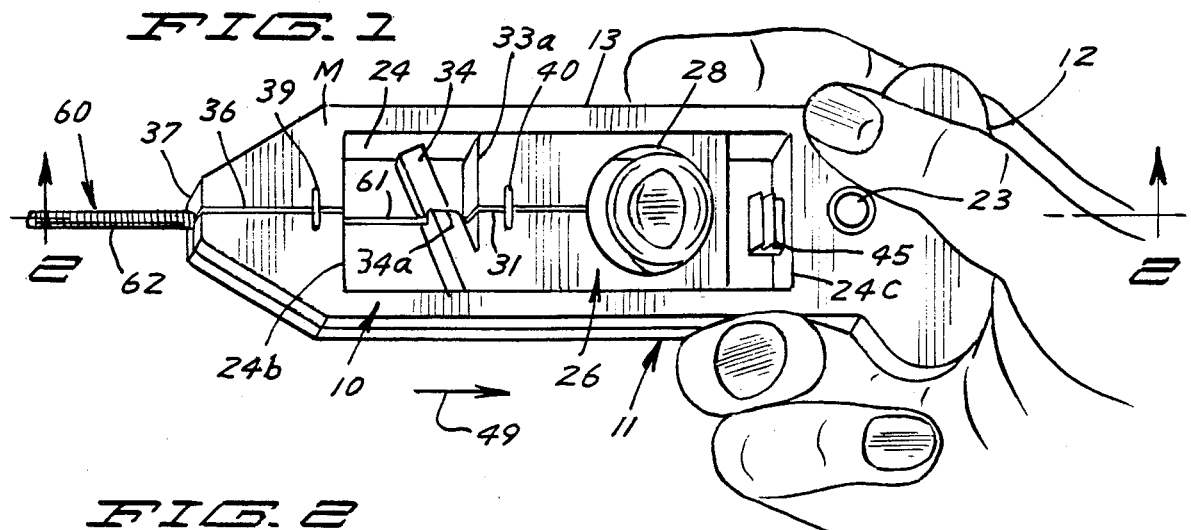
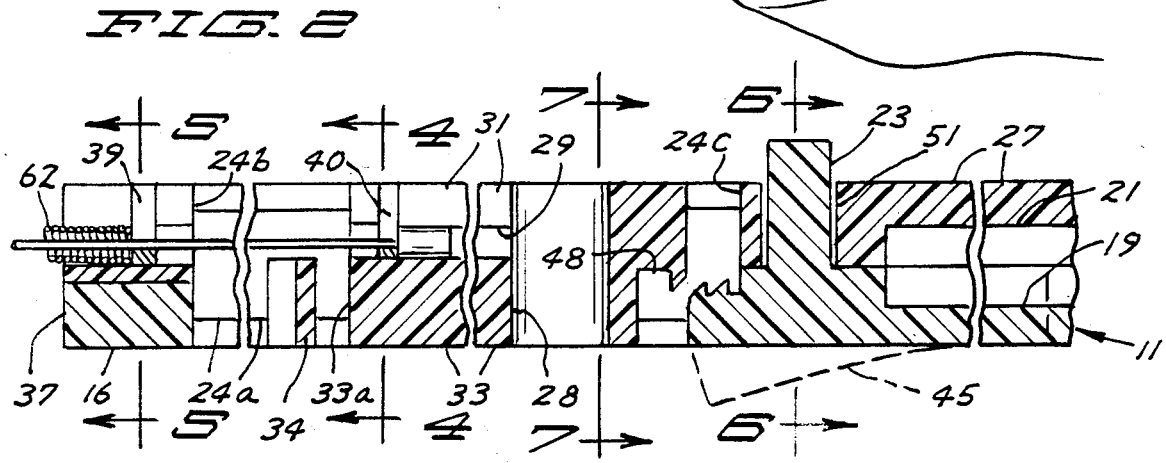
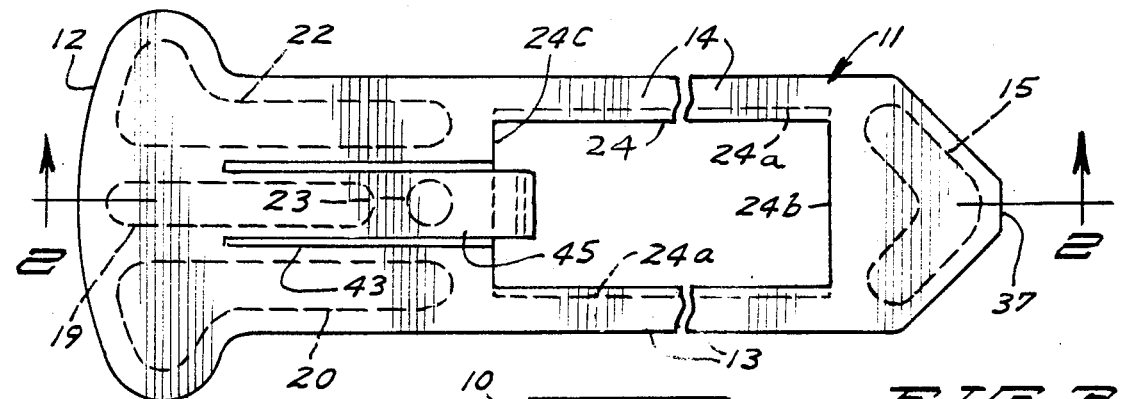
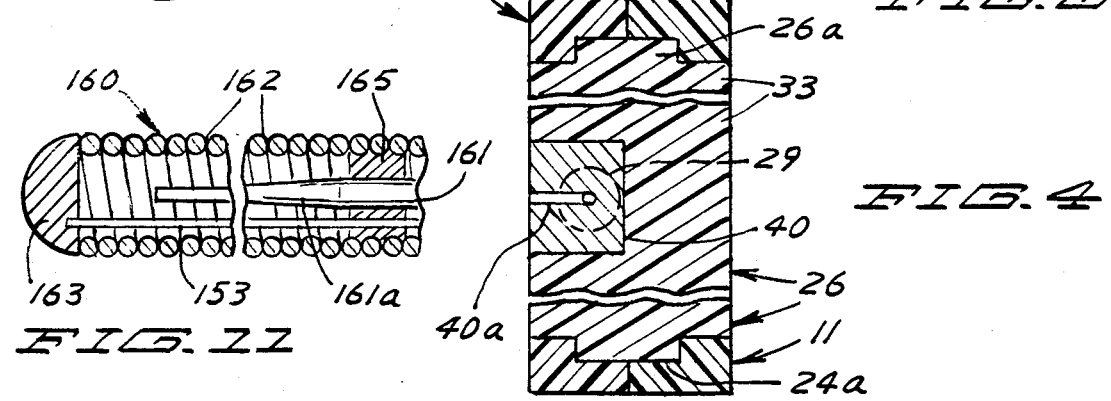

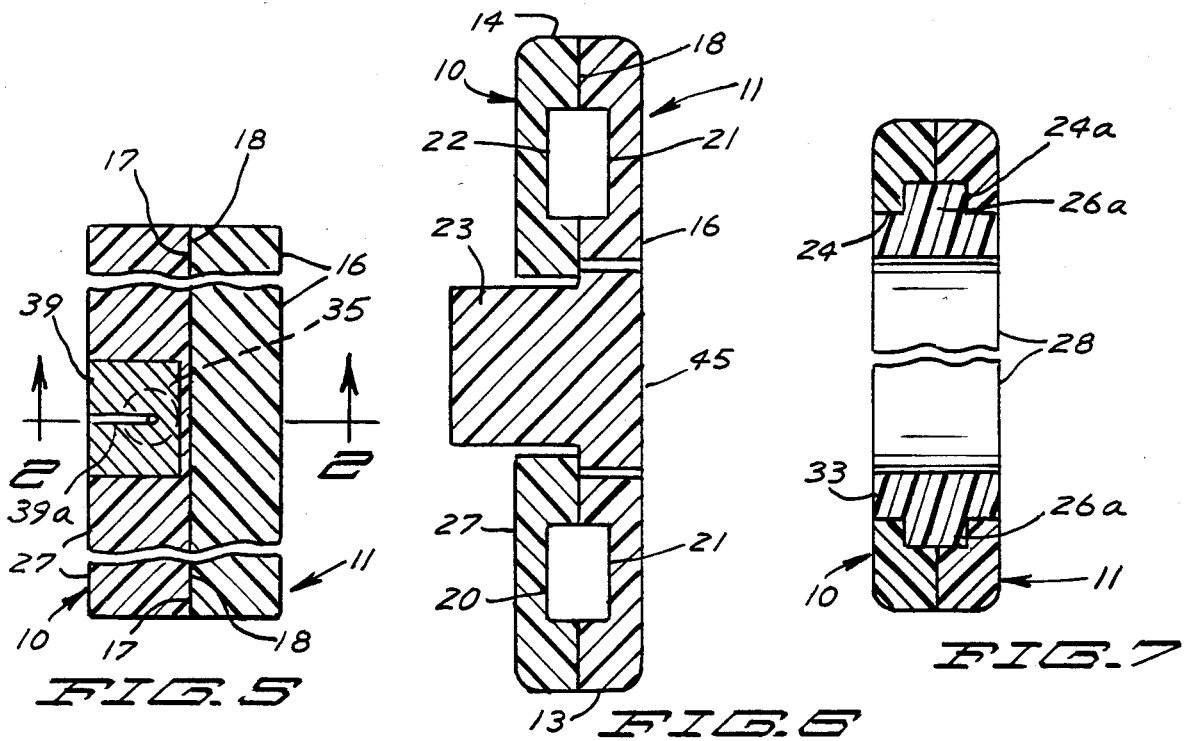
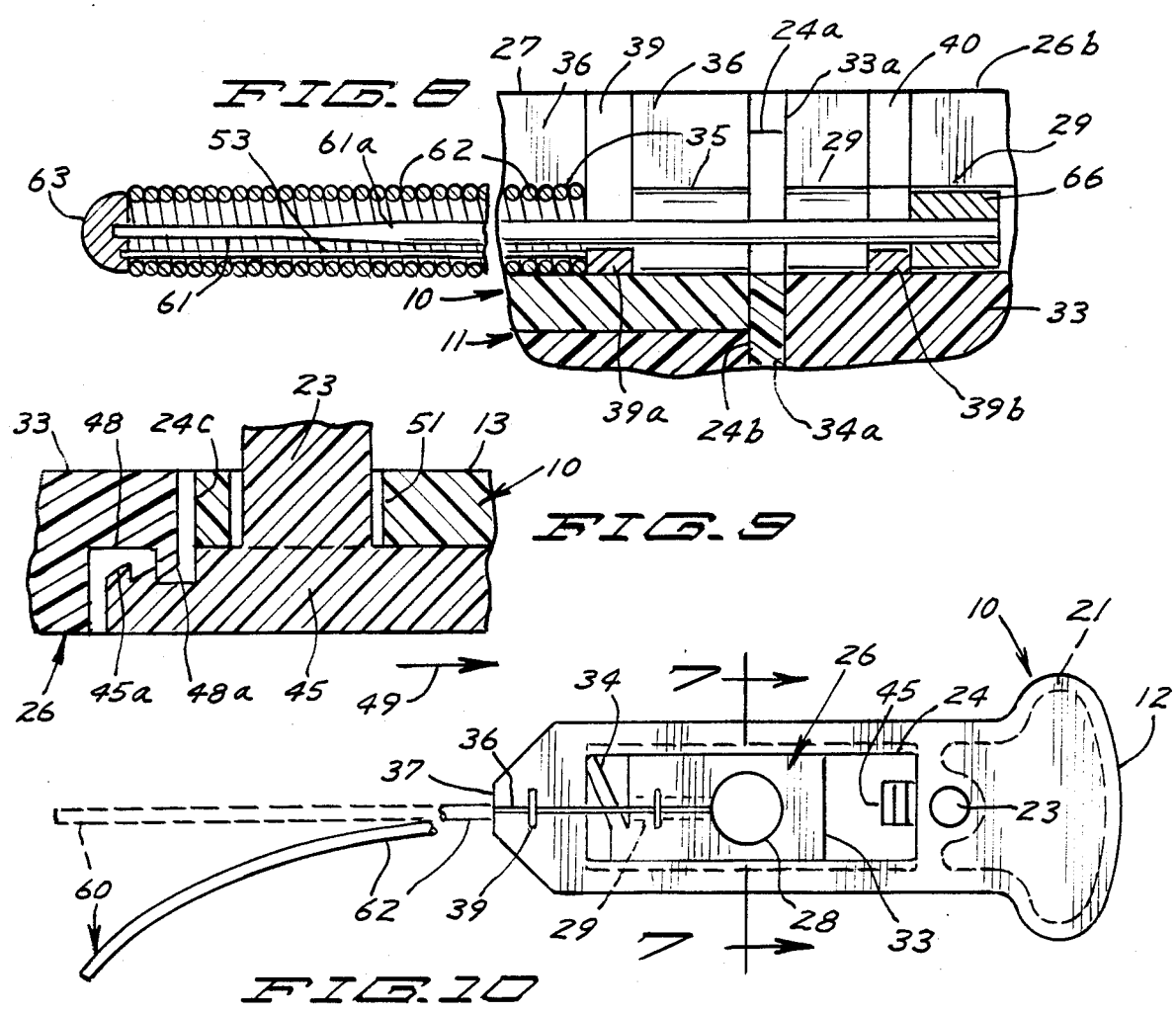

GUIDE WIRE HANDLE

BACKGROUND OF THE INVENTION

A handle for a guide wire for stiffening the guide wire and releasably retaining the guide wire in the stiffened condition.

In U.S. Pat. No. 3,847,140 to Ayella there is disclosed a spring guide handle that includes a carriage slidably mounted on a support assembly, the carriage and support assembly having slots for receiving the proximal ends of the core wire and coil spring respectively. The handle can be held and operated with one hand to manipulate the spring guide tip.

U.S. Pat. No. 3,552,384 to Pierce et al discloses a handle for a flexible controllable tip guide and includes mechanism for bending the tip and locking the tip in selected adjusted conditions. U.S. Pat. No. 4,509,945 to Kramann et al discloses a handle operable between a first position that the J-portion of a guide wire protrudes from a catheter and a second stop position the J-portion is within the catheter.

U.S. Pat. No. 4,600,014 to Beraha discloses a biopsy needle that has a handle having a recess in the main body portion with a thumb tab in the recess and connected to a cannula for moving the cannula, a catch tab connected to the knob for releasably retaining it in a position that a stylet is retracted, a spring to urge the thumb tab to move the cannula to the cannula extended position and a spring urged latch for releasably retaining the thumb tab in the cannula retracted position.

Various other U.S. Patents disclosing apparatus for manipulating the bending of guide wires and/or catheters include Nos. 3,416,531 to Edwards, 3,452,740 to Muller, 3,521,620 to Cook, and 4,456,017 to Miles while U.S. Pat. No. 3,854,473 to Matsuo discloses a stylet for varying the flexibility of an endoscope and retaining the endoscope in various selected degrees of flexibility.

In order to make improvements in apparatus of the above general nature this invention has been made.

SUMMARY OF THE INVENTION

A guide wire handle that includes a main body mounting slide member for slidable movement between a guide wire datum condition and a guide wire stiffened condition, the main body and slide member each having groove means that is elongated in the direction of sliding movement of the slide member and opens through the top surface of the main body and the slide member respectively and toward one another, the groove means of the main body abutting against the proximal end of the guide wire coil spring and the groove means of the slide member abutting against the core wire sleeve to retain the proximal terminal ends of the spring coil and core wire in spaced relationship and the core wire in sufficient tension to releasably retain the guide wire in a connected relationship to the guide handle when the slide member is in its datum position, and the main body and slide member having cooperating latching portions for releasably retaining the slide member in the slide member guide wire stiffened position. Advantageously the slide member includes a main part to which the core wire is coupled and spring means for resiliently retaining the main part in a datum position while permitting movement of the main part from the datum position to loading position in a direction opposite movement to the stiffened position to facilitate loading the handle with the guide wire.

One of the objects of this invention is to provide a new and novel guide wire handle that can be held in one hand and has a slide member operable by a finger of the same hand from a slide member guide wire datum position to a guide wire stiffened position. In furtherance of the above object, it is another object of this invention to provide a guide wire handle having new and novel latching means that will automatically move to retain the slide member in its guide wire stiffened position and is operable by the same hand that holds the handle to release the slide member to move away from its guide wire stiffened position. Still another object of this invention is to provide a guide wire handle having new and novel means operable between a slide member datum position that the guide wire is relatively relaxed, a loading position to facilitate coupling the guide wire to the handle, and a guide wire stiffened position. A further object of this invention is to provide a new and novel guide wire handle that can easily be held and operated by one hand, is of relatively light weight and is easy to manufacture.

BRIEF DESCRIPTION OF THE DRAWINGS

FIG. 1 is a perspective view of the handle of this invention being held by a hand of the user and showing the slide member in a position intermediate its datum position and its guide wire stiffened position and a fragmentary part of the proximal portion of the guide wire;

FIG. 2 is a longitudinal cross sectional view generally taken along the line and in the direction of the arrows 2—2 of FIGS. 1, 3 and 5, other than the slide member is shown adjacent to its guide wire stiffened position, the thickness is exaggerated to facilitate the illustration of the invention, the latch is shown in its release position in dotted lines and longitudinally intermediate parts are broken away and shows the first embodiment of the guide wire;

FIG. 3 is a bottom view of the base section of the handle with a longitudinally intermediate portion broken away;

FIG. 4 is a transverse cross sectionl view generally taken along the line and in the direction of the arrows 4—4 of FIG. 2 with the thickness exaggerated;

FIG. 5 is a view corresponding to FIG. 4 other than it is generally taken along the line and in the direction of the arrows 5—5 of FIG. 2;

FIG. 6 is an enlarged transverse cross sectional view generally taken along the line and in the direction of the arrows 6—6 of FIG. 2;

FIG. 7 is a transverse cross sectional view that is generally taken along the line and in the direction of the arrows 7—7 of FIG. 2 with a transverse intermediate part broken away;

FIG. 8 is an enlarged fragmentary cross sectional view showing a part of the structure in FIG. 2 other than the slide member is in its datum position and the entire intermediate portion of the guide wire is not shown;

FIG. 9 is an enlarged fragmentary longitudinal cross sectional view showing the latch in a latched position in the slide member guide wire stiffened position;

FIG. 10 is a somewhat plan view of the handle and the guide wire with the slide member and guide wire in the slide member datum position in solid lines and the guide wire in the slide member stiffened position in dotted lines, a substantial portion of the guide wire intermediate portion being broken away; and FIG. 11 is a fragmentary longitudinal cross section view of the distal end portion of the second embodiment of the guide wire with a a longitudinal intermediate portion broken away

DETAILED DESCRIPTION OF THE PREFERRED EMBODIMENTS

The guide wire handle of this invention includes a main body M having a top section, generally designated 10, and a base section, generally desingated 11, which in an assemblied condition in plan view, at the front, is of an isoscles trapezpidal shape, intermediate the isoscles part and the rear part is rectangular, and at the rear has a somewhat oval shaped part with its major (transverse) axis greater than the transverse width of the rectangular part. The oval shaped part has a rear edge 12 arcuately curved to comfortably abut against the palm of the hand of the user adjacent to the juncture of the thumb with the remainder of the hand while part of the thumb abuts against the top surface of the oval part and the adjacent portion of the rectangular part. The rectangular part has longitudinal edges 13, 14 in abutting relationship with the adjacent parts of the crooked index finger and the middle finger respectively when the handle is used to manipulate the guide wire. The longitudinal length of the rectangular part is much greater than the transverse width thereof, for example, advantageously more than twice as great. Further the top surface 27 of the top section and the bottom surface 16 of the base are substantially planar and parallel to one another. Also adjacent surfaces 17, 18 of the top and bottom sections are substantially planar and parallel other than for stud 23, part of latch 45, parts of wall portions that define opening 24 and the recesses referred to below. Recesses 15, 22, 19, 20 are formed in the bottom section to open through surface 18 while a recess 21 is provided in the top section to open through surface 17. These recesses are provided to reduce the weight of the handle. The top and base sections are secured together, for example, adhesively adhered or by the use of screws, after the slide member that will be described below is mounted by the main body. The rectangular part of the main body has wall porportions defining the longitudinally elongated rectangular opening 24 that extends vertically therethrough. The above mentioned wall portions include transversely opposite longitudinally extending eall portions vertically intermediate the main body top and bottom surfaces 27, 16 that form channel shaped tracks 24a opening toward one another. A slide member, generally designated 26, is located in the opening 24 and includes a generally rectangular shaped main part 33 that is of a substantially greater longitudinal length that its width, but of a length substantially less than the length of the opening 24. The transverse opposite sides of the main part have tongues 26a extended into the tracks to retain the slide member in opening 24 while permitting longitudinal reciprocal movement of the slide member relative to the main body. A transversely elongated spring finger 34 is at one end integrally joined to one front corner of the main part to, when not abutting against the main body, extending transversely and forwardly of the main part such as shown in FIG. 1. It is to be understood that in place of a finger being integrally joined to the main part 33, a separate leaf or coil spring could have one end secured to the main body to result in a separate finger functioning in the same manner as finger 34.

A finger hole 28 is formed in the rear portion of the slide member main part to extend vertically therethrough. A longitudinal bore 29 is formed in a vertical intermediate portion of the main part to open through the front edge 33a of the main part and to the finger hole 28. A longitudinal groove (slit) 31 likewise extends from edge 33a to bore 28 and along its length opens to bore 29 and through the top surface 26b of the slide member. Further the spring finger is provided with a top rectangular cut out that extends transversely from about the midportion thereof to the finger terminal end that is remote from where the finger is integrally joined to the slide main part such that the core wire of the guide wire described hereinafter will not abut against the spring finger, regardless of whether the spring finger is in its fully relaxed position of FIGS. 1 and 2, or is fully compressed in the loading position of FIG. 8 where the slide member is in its forwardmost guide wire loading position.

A longitudinal bore 35 is formed in the vertically intermediate portion of the main body in transverse and vertical alignment with bore 29 to open to the cut-out of the spring member and through the front edge 37 of the main body. A longitudinal groove (slit) 36 extends the length of bore 35 and opens to bore 35 and through the top surface of the main body. Advantageously groove 36 and bore 35 are provided in the top section of the main body.

A metal plate 39 is mounted in the top section intermediate edge 37 and the main body wall portion defining the front edge 24b of opening 24, and a metal plate 40 is mounted in the slide member main part intermediate its front edge 33a and the finger hole 28. The plates 39, 40 have upwardly opening slots 39a, 40a that extend downwardly to open to bores 35, 29 respectively and are located longitudinally intermediate the ends of the respective bore.

The base section 11 has a pair of parallel longitudinal slits 43 opening through the rear edge 24c of the wall portions that defines the rear end of opening 24 and extends a major portion of the distance from edge 24c to the longitudinal adjacent portion of main body edge 12 to in part define the side edges of the latch finger 45. The rear end of the latch finger is integrally joined to the oval portion of the base section. The latch finger extends forwardly of edge 24c and has two upwardly extending catch portions 45a forwardly of an upwardly opening recessed portion of the front part of the latch finger that extends forwardly of edge 24c.

The slide member has a downwardly and rearwardly opening recess 48 formed in the rear portion thereof. The recess and catch portions are of relative shapes that as the slide member is moved in a rearward direction ( arrow 49) it will have the downwardly extending protrusion 48a abut against the upwardly and rearwardly beveled surface of each catch portion to force the front portion of the latch finger to resiliently bend downwardly, and when the rear edge of the slide member abuts against or is very closely adjacent to the rear edge 24c, the finger resiliently bends such that the catch portions snap back to have one of their rear vertical surface abut against the front surface of the protrusion 48a to latchingly lock the slide member in its rearward guide wire stiffened position. With reference thereto the main body may be made of plastic of appropriate resiliency that the latch finger will bend as described herein while the remainder of the main body will not bend any signficant amount during use.

To facilitate moving the latch finger to its dotted line position of FIG. 2, the stud 23 is integrally joined to the latch finger longitudinally intermediate the catch portions and the latch finger rear end and rearwardly of edge 24c to extend upwardly through an aperture 51 formed in the top section 10. The stud in its solid line slide member locking position of FIG. 9 extends sufficiently above the top surface of the top section that prior to, or at the time, the stud is manually depressed by the thumb of the hand holding the handle to the level of the top surface of the top section, the top edges of the catch portions are below the lower horizontal edge of the protrusion, i.e. in the latch finger bent slide member release position which is indicated in dotted lines in FIG. 2.

Referring to FIGS. 1, 2 and 8, the first embodiment of the guide wire, generally designated 60, has a core wire 61 and a coil spring 62 that are connected at their distal ends by a bead 63. Preferrably the axial portion of the core wire adjacent to the bead 63 is convergingly tapered at 61a toward the bead so that the distal end portion of the guide wire is substantially more flexible than the remainder of the guide wire. In a fully relaxed condition the proximal end of the core wire extends a short distance outwardly (rearwardly) of the proximal terminal end of the coil spring. Advantageously the guide wire 60 includes a safety wire 53 that has its distal end joined to bead 63 and its proximal end joined to the proximal end portion of the coil wire.

The diameter of the proximal end portion of the core wire, other than for the sleeve 66 (or enlarged proximal terminal end of the core wire), is smaller than the minimum transverse dimension of grooves 31, 36 which in turn is smaller than the diameters of bores 35, 29. The sleeve is of a diameter greater than the transverse dimensios of the grooves, but smaller than that of the bores 29,35 as is the outer diameter (coil diameter) of the coil spring. The transverse spacing of the vertical legs of the plates 39, 40 the defines the plate slots 39a, 40a is greater than the diameter of the proximal end portion of the core wire, but is less than the diameter of the sleeve. The diameter of each of bores 35, 29 is greater than the outer diameter of the coil spring and the diameter of sleeve 66 respectively. The plates serve as stops to limit the movement of the coil spring and sleeve in the bores 35, 29 respectively toward one another. Further the spring finger cut-out is of a size so as not to frictionally engage the core wire to impede the movement of the spring finger between the slide member loading and datum positions.

In order to load the handle with the guide wire, preferrably the spring member main part is manually moved forwardly so that the front and rear edges of the spring finger along nearly their entire transverse dimensions abut against the edges 24b of the opening 24 and 33a of the main part respectively (load position of FIG. 8), and if not already in a proper relative location, the proximal terminal end of the coil spring is manually move away from the sleeve a sufficient distance that the length of core wire between the terminal end and the sleeve can be moved downwardly through the groove 31, 36 and slots 39a, 40a and into the bores 29, 35. As the sleeve is moved away from the coil spring proximal terminal end the spring is compressed and the safety wire, if provided, flexes relative to the coil spring. The coil spring is released so that the coil spring proximal end portion moves rearwardly into bore 35 to abut against plate 39 and the sleeve moves forwardly into bore 29 to abut against plate 40, or if the release of the coil spring does not result in the coil spring and sleeve abutting against the respective plate, the manual release of the slide member and the resilient action of the spring finger returning the main part 33 to its datum position of FIG. 10 will result in the coil spring and sleeve abutting against the respective plate. With the slide member in its datum position the degree of compression of the coil spring is sufficient to retain the coil spring and sleeve in abutting relationship to the respective metal plate 39, 40 while the relative widths of slits 36, 31 and the outer diameter of the coil spring and the diameter of the sleeve preclude the movement of the coil spring and the core wire sleeve upwardly through the slits 36, 31. Thus the guide wire is retained coupled to the handle as long as the proximal end portion of the core wire and the sleeve are longitudinally adjacent to the respective metal plate 39, 40.

While the slide member is in its datum position and the coil spring and sleeve abutting against the plates the distal end portion of the guide is relatively relaxed (guide wire datum position) such that the distal end portion of the guide wire may be easily bent and will remain in the arcuately curved condition if no external pressure is applied to straighten it, but at the same time the sleeve and coil proximal terminal end are retained in abutting relationship to the plates 39, 40 due to the resilient action of the coil spring. Further, in the datum position, plates 39, 40 are sufficiently spaced from edge 37 and the adjacent part of the finger hole respectively to prevent the coil spring and sleeve moving out of the respective bore.

With the guide wire coil abutting against plate 39 and the sleeve abutting against plate 40 and the slide member in its datum position, the degree of compression of the coil spring is insufficient to stiffen the guide wire. That is the distal end portion of the guide wire is relatively limp and if arcuately curved, or if moved to be arcuately curved, when laying on a table, will remain in such an arcuately curved condition until the distal end portion is manually moved or the slide member is moved away from and rearwardly of its datum position. However if the slide member is moved rearwardly and locked in its guide wire stiffened position, the distal end portion of the guide wire is substantially straight (stiffened) and if manually moved into an arcuately curved condition, upon being manually released, will snap back into its straightened condition.

With the handle grasped as previously described and shown in FIG. 1 and the middle finger extended at least partially through the finger hole 28 the palm of the hand holds the main body against rearward movement (arrow 49), the slide member is moved rearwardly from its datum position to increase the degree of spring compression and tension in the core wire, the flexibility of the distal end portion of the core wire decreases. That is the distal end portion as well as te rest of the guide wire becomes stiffer. By moving the slide member forwardly and rearwardly the flexibility of the guide wire distal end portion can be controlled as the guide wire is moved into and through a body vessel, for example, into a selected artery branch, or other body lumen. When it is desired to retain the distal end portion of the guide wire in its stiffened (rigid) condition, the slide member is moved rearwardly to abut against edge 24c and the latch finger first moves to its release position and then snaps back into place to retain the slide member in its guide wire stiffened condition. Now the handle may be placed on a table, or etc., allowing the user to use both hands for other purposes until such time as it is desired to decrease the rigidity of the guide wire. To decrease the rigidity (stiffness), the stud 23 is depressed; and due to the spring action of the guide wire the slide member resiliently moves forwardly, unless manually prevented from doing so.

Due to the provision of the finger hole and stud 23, and the size and shape of the handle, one finger can be used to move the slide member while the thumb of the same hand can be used to depress the stud. Accordingly only one hand is needed to hold and operate the handle, including operating the latch finger to its release position.

In place of using plates 39, 40, the adjacent portions of bores 35, 29 between the plates may be made of smaller diameters, but still be larger than the proximal end of the wire, to provide oppositely facing bore shoulders that perform the same functions as the plates. However, in the event the main body and slide member are mde of plastic, the durability would not be as great as with the metal plates. The slide member wall portions defining the core wire bore and plate 40,(or if no plate 40 used the slit and bore of two different diameters as referred to above) provide coupling means for attaching the core wire proximal end portion and sleeve to be moved rearwardly with the slide member.

Also, in place of plates 39, 40, metal clips may be used that have web portions in the bottom parts of the respective bore 35, 29 and vertical legs spaced to permit the core wire being moved downwardly therebetween while limiting the movement of the coil spring and sleeve toward one another as described above.

Although a ball shaped knob of the same diameter as the sleeve may be used in place of the sleeve, it is preferred a sleeve be used. That is after the distal ends of the core wire and coil spring have been joined by the bead; in the relaxed condition the spacing of the proximal terminal ends of the coil spring and core wire may vary. To obviate such variations the sleeve is slid onto the proximal end portion until the sleeve end that is adjacent to the coil spring in the coil spring relaxed condition is a preselected distance from the coil spring proximal terminal end and then the sleeve is soldered or otherwise suitably fixedly joined to the core wire. Any part of the core wire then extending rearwardly of the sleeve may be trimmed away.

In place of the guide wire 60 there may be provided a second embodiment of a guide wire, generally designated 160 that is of the same construction other than for the differences noted hereinafter. In place of the core wire being joined to the bead 163, which is joined to the distal ends of the coil spring 162 and safety wire 153, the distal tapered portion 160a of the core wire terminates longitudinally intermediate the bead 163 and a brazed joint 165 joins the distal end portion of the non-tapered part of the core wire and safety wire to one another and to the coil spring. The brazed joint may be about 2 to 3 cm. from the bead 163. The operation of the guide handle with the guide wire 160 would be the same as that with guide wire 60.

In place of the coil spring extending substantially the entire length of the guide wire, just the front part may be provided with a coil spring and the rearward part of the core wire would extend through a stainless steel tubing or tubing of other suitable material which has its rear end abutting against plate 39 and at its distal end suitably mounts the proximal end of the coil spring to have the core wire extend thereinto. Further the guide handle may be used when tubing is substituted for the entire length of the coil spring to stiffen the tubing, provided the tubing was suitably compressable and would stiffen when the tension in the core wire is increased. The terminology coil spring used in the claims is intended to cover modifications as set forth in this paragraph.

Advantageously the main body and latch finger are made of materials that are semi-rigid so that no significant bending of the main body takes place while the slide member is moved from its datum position to its rear position to progressively increase the tension in the core wire and thereby the stiffness of the guide wire, but the base and latch finger are of sufficient resiliency to permit the latch finger being operated between its positions as has been described.

Although it is preferred that the slide member include, or there is provided, spring means for resiliently retaining the slide member in a datum position whereby the slide member main part is movable a limited amount in a forward direction from its datum position such as previously described, the handle can be made without such spring means (spring finger. In such an event the slide member datum position would correspond to the loading position previously described (main part front edge 33a abutting agains edge 24b) and the longitudinal spacing of the metal plates and/or the axial spacing of the core wire sleeve and the coil spring proximal terminal end would be such that in the thus modified datum position the core wire would be under slight tension to retain the guide wire coupled to the modified guide wire handle.

As an example of the invention, but not otherwise as a limitation thereon, the main body, slide member and latch finger of one embodiment may be made of a polysulphone material, the maximum length of the handle of 6", the transverse spacing of edges 13, 14 about 1.3", the movement of the slide member in the slide opening about 0.8", the maximum thickness of the top section about 0.25", the length of the latch finger about 1.3", the maximum thickness of the slide member about $\frac{1}{4}$" and the maximum movement of the terminal end of the spring finger away from the main part about $\frac{1}{8}$". The term maximum as used in this paragraph does not mean other embodiments can not be made of larger dimensions.

Even though it is preferred and the invention has been described with the latch finger being integrally joined to the remainder of the main body, it is to be understood the latch finger could be formed as a separate member of the same or similar shape as member 45 and mounted by the main body to be spring urged to the latched position to function in the same manner as latch finger 45, i.e. movable by a stud 23 joined thereto to the slide member release position and resiliently retained in a slide member locked position.

Even though the main body has been described as being made of two sections, it can be made of a single top section without having a generally planar bottom surface, but still of a thickness many times smaller than the maximum transverse dimension which in turn is a number of times smaller than its length.

Also, even though the handle of this invention has been described as a guide wire handle it is to be understood it can be used as a manipulator handle for operating other type of medical devices. For example, the handle may be used for manipulating a forceps of a general nature such as disclosed in U.S. Pat. No. 4,632,110 to Sanagi with the proximal end of the coil spring sheath abutting against plate 39 and the proximal end of the control being appropriately shaped and abutting against plate 40. The slide member 26 would be retracted to close the forcep cups and moved, or allowed to move, forwardly to open the cups. Thus the handle can be used to manipulate a core wire that is extended through a tubular member of a medical device and is longitudinally movable relative to at least a major portion of the length of the tubular member.

What is claimed is:

1. For manipulating a medical device such as a guide wire or the like and mounting the proximal end portion of a guide wire wherein the guide wire includes a coil spring and a core wire which have distal end portions and the coil spring has a proximal terminal end portion and the core wire has a proximal end portion and an enlarged terminal end joined to the proximal end portion, a manipulator handle that includes a longitudinally elongated main body having a front and a rear end portion, a slide member longitudinally movably mounted on the main body for movement between a datum guide wire relaxed position to a guide wire stiffened rear position, one of the slide member and the main body having a latch member that is resiliently retained in its latching position and is resiliently movable between a release position and a latching position latchingly engaging the other of the slide member and the main body to retain the slide member in its rear position, the other of the slide member and the main body having a portion to be latchingly engaged by the latch member for retaining the slide member in the slide member rear position, manually movable means joined to the latch member for moving the latch member to its release position, the slide member having coupling means for couplingly engaging the core wire enlarged end and moving the coil wire proximal end portion therewith when the slide member is moved toward the main body rear end portion and the main body having coil spring retaining means for engaging and blocking transverse and rearward movement of the coil spring proximal end portion when the coil spring proximal end portion is engaged thereby and the core wire enlarged end is couplingly engaged by the coupling means.

2. The apparatus of claim 1 further characterized in that each of the slide member and main body have a top surface, an opposite surface and a front edge, that the retaining means includes a longitudinally extending bore intermediate the main body top and opposite surfaces and opening to the main body top and opposite surfaces and opening to the main body frton edge and toward the slide member to have the core wire proximal end portion extend therethrough and to the slide member coupling means, and wall portions defining a slit extending the length of the main body bore and opening thereto along the main body bore length, and through the main body top surface along the length of the slit, the main body bore having at least a front end portion of a diameter greater than the coil spring proximal end portion outer diameter and the main body slit being of a transverse dimension smaller than the coil spring outer diameter.

3. The apparatus of claim 1 further characterized in that each of the main body and slide member has top and bottom surfaces, that the main body has wall means defining a slide member opening that opens through the top and bottom surface and has an opening rear edge, and means for mounting the slide member for slidable movement, including to the slide member rear position which is adjacent to the opening rear edge, the latch member in its latching position extending forwardly of the opening rear edge and into the opening.

4. The apparatus of claim 1 further characterized in that the slide member includes a main part that has the coupling means and is manually movable a limited amount toward the main body front end portion from the slide member datum position to a guide wire loading position and spring means acting between the main part and the main body to resiliently urge the main part from the main part loading position to the slide member datum position.

5. The apparatus of claim 4 further characterized in that the main body has wall means defining a slide member opening that mounts the slide member for longitudinal movement, including front wall means defining an opening front edge and that the spring means includes a spring finger joined to the main part to engage said front edge when the main part is in the main part loading position and the slide member datum position, and moves out of engagement with the front edge when the slide member is moved from the datum position toward the slide member rear position.

6. The apparatus of claim 1 further characterized in that the main body has top and bottom surfaces and wall means defining a longitudinally elongated opening extending therethrough to open through said top and bottom surfaces and transversely opposite slide member tracks to mountingly retain the slide member in said opening and permit the slide member being moved longitudinally between its positions.

7. The apparatus of claim 6 further characterized in that the latch member is a latch finger having a front end portion extended into the main body opening and a rear end portion integrally joined to the main body and being of a resiliency for being bent between the latch member positions.

8. The apparatus of claim 7 further characterized in that the slide member has top and bottom surfaces and a finger hole extending through the slide member opening through the slide member top and bottom surfaces to facilitate moving the slide member.

9. The apparatus of claim 8 wherein the handle is shaped and adapted to be held and operated by one hand of a user, further characterized in that the main body has a transversely arcuately curved rear edge adapted to abut against the user's one hand adjacent the juncture of the thumb to the remainder of the one hand and transversely opposite longitudinally extending side edge portions adapted to abut against the adjacent surface portions of the user's crooked index and ring fingers, and that the slide member hole is located to have the ring finger of the one hand extend thereinto.

10. The apparatus of claim 8 further characterized in that the slide member includes a main part that has a transverse front edge and the finger hole, that the main body has a transverse front edge, and that the coupling means includes slide member wall means defining a longitudinal bore intermediate the slide member top and bottom surfaces that opens to the finger hole and through the main part front edge and a slit that extends the length of and opens to the slide member bore and through the main part front edge, the slide member bore having at least a rear bore portion of a larger diameter than the core wire enlarged terminal end, the slit being of a transverse dimension greater than the core wire proximal end portion and smaller than the diameter of the core wire terminal end.

11. The apparatus of claim 10 further characterized in that the coupling means includes stop means extending within the slide member slit and bore for abutting against the enlarged terminal end to limit the forward movement of the enlarged terminal end in the slide member bore and that the coil spring retaining means includes main body wall portions defining a main body longitudinal bore intermediate the main body top and bottom surfaces and opening to the slide member opening and through the main body front edge and a main body slit extending the length of the main body bore and opening along its length to the main body bore and through the main body top surface, the main body bore being of a larger diameter than the coil spring coil diameter and the main body slit being of a transverse dimension smaller than the coil spring diameter and greater than the core wire diameter, and stop means extended into the main body bore and slit to limit the rearward movement of the coil spring into the main body bore.

12. For being operated and held by one hand of a user, and mounting the proximal end portion of a medical device wherein the device includes a coil spring and a core wire having connected distal end portions, the spring has a proximal end portion and the core wire has an enlarged terminal end joined to the core wire proximal end portion, a manipulator handle that includes a longitudinally elongated main body having a front end portion and a rear end portion, the main body having a transversely arcuately curved rear edge adapted to abut against the one hand of the user adjacent to the juncture of the thumb with the remainder of the hand, transversely opposite, longitudinally extending side edge portions adapted to abut against the adjacent surfaces of the crooked index and ring fingers of the one hand of the user while the main body rear edge abuts against the one hand of the user, and a slide member having a middle finger hole and being mounted on the main body for fore and aft movement between a rear guide wire stiffened position and a datum position forward of the rear position and being adapted to be moved by the middle finger of the one hand of the user while the main body abuts against the fore and ring fingers and is adjacent to the juncture of the thumb and the remainder of the one hand of the user, the main body having means abuttable against the coil spring proximal end portion to limit the rearward movement of the coil spring when the core wire is in tension, and the slide member having means for engaging the core wire terminal end and retaining the core wire in relatively slight tension when the slide member is in its datum position and the main body means limits the rearward movement of the coil spring and progressively increases the tension in the core wire when the slide member is moved toward the slide member rear position.

13. The apparatus of claim 12 further characterized in that the slide member has a latch body recess and that there is provided latch means joined to the main body for movement between a latching position extending into the latch recess when the slide member is in its rear position to selectively releasably retain the slide member in its rear position, the latch means having a portion adapted to be moved by the thumb of the one hand of the user when the main body side edge portions abuts against the fore and ring fingers and the main body rear edge abuts against the one hand adjacent the juncture of the thumb to the remainder of the one hand for moving the latch means to its release position.

14. The apparatus of claim 12 further characterized in that the main body has a top and a bottom surface and wall means defining a slide member opening that opens through the top and bottom surfaces.

15. The apparatus of claim 14 further characterized in that said wall means includes transversely opposite portions defining tracks for mounting the slide member for movement between its positions.

16. The apparatus of claim 14 further characterized in that the slide member has top and bottom surfaces and is mounted within the slide member opening, at least the major portion of the main body and slide member top surfaces being substantially coplanar, the slide member finger hole opening through the slide member top and bottom surfaces.

17. The apparatus of claim 16 further characterized in that the main body includes a base section having the main body bottom surface and a top section having the main body top surface, the latch finger being longitudinally elongated and having a rear end portion integrally joined to the base section and being resiliently movable relative to the top and base sections, the base section and latch finger being made of materials of a semi-rigidity that permits the latch finger being resiliently bent to move between its positions.

18. The apparatus of claim 14 further characterized in that the slide member has top and bottom surfaces, is mounted within the slide member opening and has a latch finger latching portion, and that there is provided a latch finger that is mounted on the main body for movement between a slide member release position and a latched position to latchingly engage the slide member finger latching portion and is resiliently retained in the latched position, and a protrusion joined to the latch finger that in the latch finger latched position extends remote from the main body top surface to a position for being moved by the thumb of the one hand of the user to in turn move the latch finger to its release position.

19. For mounting the proximal end portion of a guide wire and stiffening the guide wire wherein the guide wire includes a coil spring and a core wire which have distal end portions connected together and the coil spring has a proximal terminal end portion and the core wire has a proximl end portion and a terminal end joined to the core wire proximal end portion, a guide wire handle and stiffener comprising, a longitudinally elongated main body having a front end portion, a rear end portion, a top surface, a bottom surface and perimetric wall means defining a slide member opening that opens through the main body top and bottom surfaces, and includes an opening front edge and an opening rear edge, and a slide member mounted by the main body in the slide member opening for longitudinal slidable movement between a forward position abutting against the front edge and a rear guide wire stiffened position adjacent to the rear edge, said main body having limiting means for mounting and limiting the rearward movement of the coil spring proximal portion while permitting the core wire proximal end portion to be longitudinally movably extended into the slide member opening, and the slide member having engaging means for engaging the core wire terminal end to increase the tension in the core wire and the compression of the coil spring when the slide member is moved away from the front edge toward the rear edge and the main body limiting means limits the movement of the coil spring proximal end portion in a rearward direction.

20. The apparatus of claim 19 further characterized in that there is provided cooperating means on the slide member and main body that is manually operable for releasably retaining the slide member adjacent to the rear edge while the core wire is engaged by the slide member engaging means.

21. The apparatus of claim 19 further characterized in that the slide member has top and bottom surfaces, the slide member top and bottom surfaces having major portions that are at least nearly coplanar with at least the major portions of the main body top and bottom surfaces respectively.

22. The apparatus of claim 19 further characterized in that the slide member has a finger hole to facilitate the movement of the slide member between its positions, and has a latch engagable portion, and that latch means is mounted on the main body for engaging the latch engagable portion for releasably retaining the slide member adjacent to the opening rear edge.

23. The apparatus of claim 19 further characterized in that the slide member includes a main part having the engaging mens and being mounted by the main body for movement between a rear position that the guide wire is stiffened, a datum position tat the guide wire is relatively relaxed while the guide wire is attached to the handle and a guide wire loading position forwardly of the main part datum position to facilitate loading the guide wire on the handle, and spring means acting against the main part for constantly resiliently urging the main part to the main part datum position when the main part is forwardly of the main part datum position.

24. The apparatus of claim 23 further characterized in that the spring means includes a spring finger that abuts against the front edge when the main part is in its datum position and is moved out of abutting relationship to the front edge when the main part is moved from the main part datum position toward the main part rear position.

25. For mounting the proximal end portion of a guide wire and stiffening the guide wire wherein the guide wire includes a coil spring and a core wire which have distal end portions connected together and the coil spring has a proximal terminal end portion and the core wire has a proximal end portion and a terminal end joined to the core wire proximal end portion, a guide wire handle comprising a longitudinally elongated main body having a front end portion and a rear end portion, the main body including limiting means for mounting and limiting the rearward movement of the coil spring proximal portion while permitting the core wire proximal end portion to be longitudinally moved relative to the coil spring proximal end portion, a slide member main part mounted on the main body for longitudinal movement between a rear guide wire stiffened position, a forward guide wire loading position and a datum position intermediate the forward and rear positions that the guide wire is relatively relaxed while being in a position that the guide wire remains in a handle loaded condition relative to the main body and the main part, the slide member main part having engaging means releasably coupled to the core wire terminal end to increase the tension in the core wire and the compression of the coil spring when the main part is moved away from its datum position toward the main part rear position and the main body limiting means limits the movement of the coil spring proximal end portion in a rearward direction, and slide member spring means for resiliently urging the main part to move from the main part loading position to the main part datum position, the main part being movable to its loading position to facilitate moving the coil spring into engagement with the limiting means and the core wire terminal end to a coupled condition relative to the engaging means to couple the guide wire to the handle.

26. The apparatus according to claim 25 wherein the core wire and coil spring distal end portions each has a terminal distal end portion, and that the guide wire includes a bead that connects the coil spring and core wire distal terminal end portions together.

27. The apparatus according to claim 25 wherein the guide wire is axially elongated, the core wire and coil spring distal end portions each has a terminal distal end portion, that the core wire terminal end portion is axially spaced from the coil spring terminal end portion, and that the guide wire includes means that connects the distal end portions together which is axially spaced from the coil wire terminal end portion.

28. The apparatus according to claim 25 wherein the core wire proximal end portion and terminal end are each axially elongated, that the core wire terminal end comprises an axially elongated sleeve that is fixed to the core wire proximal end portion, is of a substantially larger outer diameter than the diameter of the core wire proximal end portion and is of an axial length many times greater than the axial length of the sleeve.

29. A guide wire comprising an axially elongated, compressable coil spring, a safety wire, a core wire, each of the coil spring, safety wire and core wire having a distal end portion and a proximal end portion, each distal end portion having a terminal distal end, first means for securing the coil spring and safety wire terminal ends in fixed relationship to one another, second means axially spaced from the first means for securing the coil spring, core wire and safety wire distal end portions together in fixed relationship, the core wire distal end being axially spaced from each of the first and second means and axially between the first and second means, the core wire distal end portion being convergingly tapered in a direction axially totoward the first means, the safety wire proximal end portion being fixedly secured to the coil spring proximal end portion, the safety wire and core wire extending within the coil spring, and third means of a larger diameter than the core wire secured to the core wire proximal end portion that is movable independent of the coil spring proximal end portion for transmitting a force through the core wire and second means to the coil spring to compress the coil spring for increasing the rigidity of the guide when pulled axially in a direction away from the first means, the third means extending a short distance more remote from the second means than the coil proximal end portion when the coil spring is in its fully relaxed condition, the core wire between the second and third means being axially movable relative to the coil spring, including the coil spring proximal end portion for transmitting said force.

* * * * *